(12) United States Patent
Doxsey et al.

(10) Patent No.: US 7,682,799 B2
(45) Date of Patent: Mar. 23, 2010

(54) CELL DIVISION MARKER

(75) Inventors: Stephen J. Doxsey, Princeton, MA (US); Chun-Ting Chen, Worcester, MA (US)

(73) Assignee: University of Massachusetts, Boston, MA (US)

( * ) Notice: Subject to any disclaimer, the term of this patent is extended or adjusted under 35 U.S.C. 154(b) by 330 days.

(21) Appl. No.: 11/544,053

(22) Filed: Oct. 6, 2006

(65) Prior Publication Data

US 2007/0154957 A1   Jul. 5, 2007

Related U.S. Application Data

(60) Provisional application No. 60/724,093, filed on Oct. 6, 2005.

(51) Int. Cl.
*G01N 33/53* (2006.01)

(52) U.S. Cl. .................. 435/7.1; 435/1.1; 435/6; 435/7.21; 435/40.5; 435/40.51; 435/40.52; 435/354; 435/358; 435/363; 435/367; 435/376; 436/63; 436/164; 436/172

(58) Field of Classification Search .......... 435/1.1, 435/6, 7.1, 7.2, 7.21, 7.23, 7.24, 7.92–7.95, 435/40.5, 40.51, 40.52, 354, 358, 363, 367, 435/371, 372, 373, 374, 376, 973; 436/512, 436/517, 519, 63, 64, 164, 172, 813

See application file for complete search history.

(56) References Cited

U.S. PATENT DOCUMENTS

| 7,005,252 | B1 | 2/2006 | Thomson | |
|---|---|---|---|---|
| 2004/0029157 | A1* | 2/2004 | Tatsuka et al. | 435/6 |
| 2005/0191639 | A1 | 9/2005 | Contreras et al. | |
| 2005/0208058 | A1 | 9/2005 | Doxsey et al. | |
| 2008/0063638 | A1* | 3/2008 | Einat et al. | 424/130.1 |

FOREIGN PATENT DOCUMENTS

| WO | WO 01/66697 | 9/2001 |
|---|---|---|
| WO | WO 03/045988 | 6/2003 |

OTHER PUBLICATIONS

Lee et al., Plk Is an M-Phase-Specific Protein Kinase and Interacts with a Kinesin-Like Protein CHO1/MKLP-1, Molecular and Cellular Biology 15 (12): 7143-7151 (Dec. 1995).*

Chang et al., δ-tubulin and ε-tubulin: two new human centrosomal tubulins reveal new aspects of centrosome structure and function, Nature Cell Biology 3: 30-35 (Jan. 2000).*

(Continued)

*Primary Examiner*—Gailene R Gabel
(74) *Attorney, Agent, or Firm*—Fish & Richardson P.C.

(57) ABSTRACT

This application relates to a newly identified animal cell structure, the midbody scar. This structure is a remnant of the midbody that is retained by one daughter cell following cytokinesis and persists through multiple subsequent cell cycles. The midbody scar can be useful as a marker of dividing cells or of a cell's replicative age.

12 Claims, 4 Drawing Sheets
(4 of 4 Drawing Sheet(s) Filed in Color)

OTHER PUBLICATIONS

Fabbro et al., Cdk1/Erk2- and Plk1-Dependent Phosphorylation of a Centrosome Protein, Cep55, Is Required for Its Recruitment to Midbody and Cytokinesis, Developmental Cell, 9 (4): 477-488, (Oct. 1, 2005).*

Bell and Van Zant, "Stem cells, aging, and cancer: inevitabilities and outcomes," *Oncogene*, 23:7290-7296 (2004).

Chang and Stearns, "Delta-tubulin and epsilon-tubulin: two new human centrosomal tubulins reveal new aspects of centrosome structure and function," *Nat. Cell Biol.*, 2:30-35 (2000).

Chen et al., "Centrosomal anchoring of protein kinase C betaII by pericentrin controls microtubule organization, spindle function, and cytokinesis," J. Biol. Chem., 279:4829-39 (2003).

Doxsey, "Centrosomes as command centres for cellular control," *Nat. Cell Biol.*, 3:E1-E3 (2001).

Doxsey., "Molecular links between centrosome and midbody," *Mol. Cell*, 20:170-172 (2005).

Fabbro et al., "Cdk1/Erk2- and Plk1-dependent phosphorylation of a centrosome protein, Cep55, is required for its recruitment to midbody and cytokinesis," *Dev. Cell*, 9:477-488 (2000).

Glotzer, "Animal cell cytokinesis," *Annu. Rev. Cell Dev. Biol.*, 17:351-386 (2001).

Glotzer, "The molecular requirements for cytokinesis," *Science*, 307:1735-1739 (2005).

Gromley et al., "A novel human protein of the maternal centriole is required for the final stages of cytokinesis and entry into S phase," *J. Cell Biol.*, 161:535-545 (2003).

Gromley et al., "Centriolin anchoring of exocyst and SNARE complexes at the midbody is required for secretory-vesicle-mediated abscission," *Cell*, 123:75-87 (2005).

Gromley et al., "Centriolin-anchoring of exocyst and SNARE complexes at the midbody is required for localized secretion and abscission during cytokinesis," *Mol. Biol. Cell*, 15(suppl.):205a (abstract only) (2004).

Guertin et al., "Cytokinesis in eukaryotes," *Microbiol. Mol. Biol. Rev.*, 66:155-178 (2002).

Jordan et al., "Cancer Stem Cells," *N. Eng. J. Med.*, 355:1253 (2006).

Kuriyama and Ensrud, "Obtaining antibodies to spindle components," *Methods Cell Biol.*, 61:233-244 (1999).

Marx, "Cancer research. Mutant stem cells may seed cancer," *Science*, 301:1308-1310 (2003).

Skop et al., "Dissection of the mammalian midbody proteome reveals conserved cytokinesis mechanisms," *Science*, 305:61-66 (2004).

Xu et al., "Basic FGF and suppression of BMP signaling sustain undifferentiated proliferation of human ES cells," *Nat. Methods*, 2:185-90 (2005).

Zhao et al., "Cep55, a microtubule-bundling protein, associates with centralspindlin to control the midbody integrity and cell abscission during cytokinesis," *Mol. Biol. Cell*, 17:3881-3896 (2006).

Zipori, D., "The nature of stem cells: state rather than entity," *Nat. Rev. Genet.*, 5:873-878 (2004).

Kuriyama et al., "CHO1, a mammalian kinesin-like protein, interacts with F-actin and is involved in the terminal phase of cytokinesis," J. Cell Biol., 156:783-790 (2002).

Matuliene et al., "Kinesin-like protein CHO1 is required for the formation of midbody matrix and the completion of cytokinesis in mammalian cells," Mol. Biol. Cell, 13:1832-1845 (2002).

Mishima et al., "Central spindle assembly and cytokinesis require a kinesin-like protein/RhoGAP complex with microtubule bundling activity," Dev. Cell, 2:41-54 (2002).

Aumais et al., "Role for NudC, a dynein-associated nuclear movement protein, in mitosis and cytokinesis," *J. Cell Sci.*, 166:1991-2003 (2003).

Guse et al., "Phosphorylation of ZEN-4/MKLP1 by Aurora B regulates completion of cytokinesis," *Curr. Biol.*, 15:778-786 (2005).

Katayama et al., "The Aurora kinases: Role in cell transformation and tumorigenesis," *Cancer Metastasis Rev.*, 22:451-464 (2003).

Extended European Search Report for App. Ser. No. EP 06 83 6218, mailed Oct. 7, 2009, 7 pages.

* cited by examiner

Figure 1A 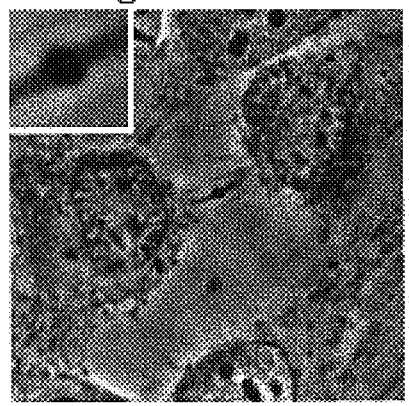 Figure 1B 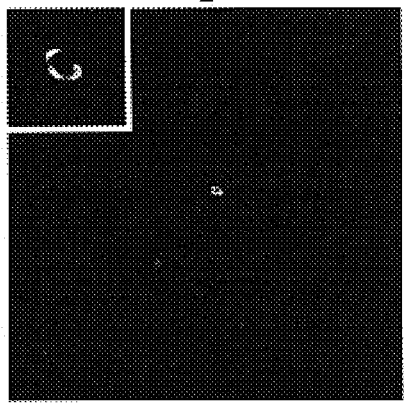
Figure 1C 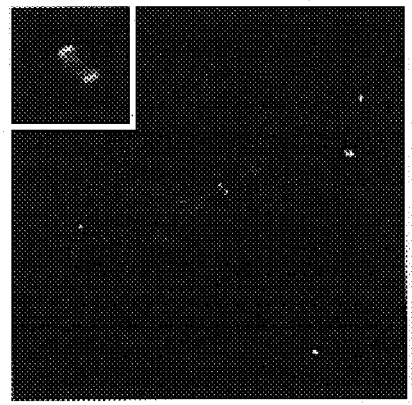 Figure 1D
Figure 1E
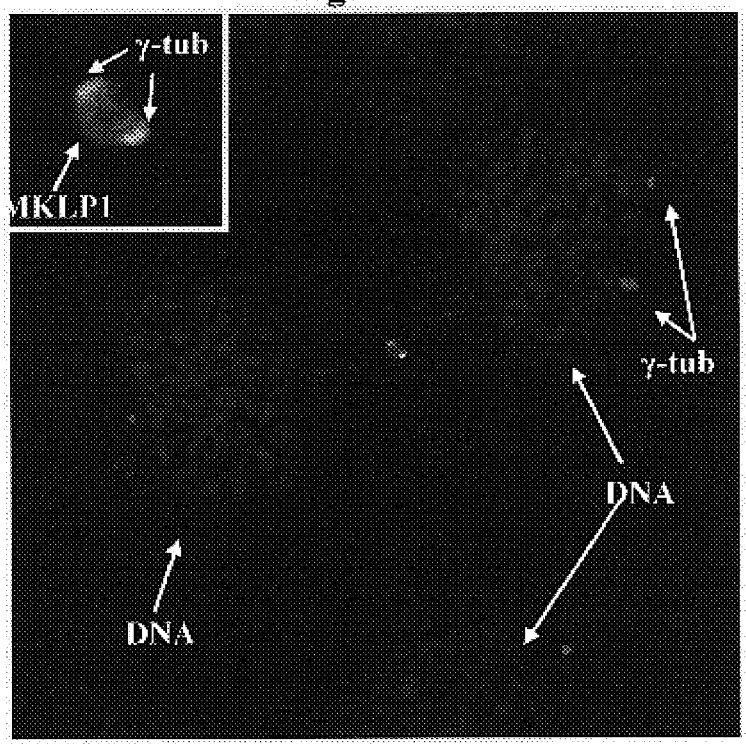

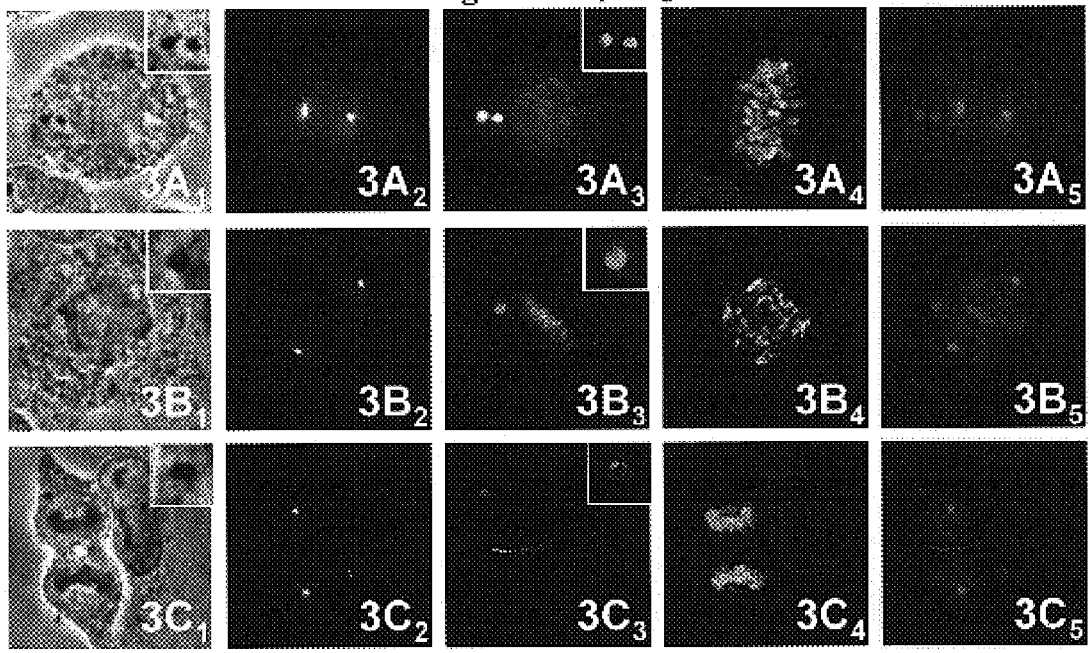
Figures 3A₁-3C₅

CELL DIVISION MARKER

CLAIM OF PRIORITY

This application claims the benefit under 35 USC §119(e) of U.S. Provisional Patent Application Ser. No. 60/724,093, filed on Oct. 6, 2005, the entire contents of which are hereby incorporated by reference.

STATEMENT OF FEDERALLY SPONSORED RESEARCH

This invention was made with Government support under grant number GM51994 awarded by the National Institute of Health. The Government has certain rights in the invention.

BACKGROUND

The mechanisms behind aging and longevity are a current topic of investigation. Much progress has been made studying the genetics of cellular aging in yeast. Yeast cell divisions produce a detectable remnant on the cell wall of the mother cell, known as a bud scar. Cellular aging in yeast is related to the number of daughter cell progeny a cell has produced. By counting the number of bud scars on the mother cell wall, the number of divisions, and thus the age of the cell, can be determined. A similar marker of previous cell divisions would be useful for studies of cellular aging in mammals.

SUMMARY

The invention is based, inter alia, on the discovery of a cellular structure in animal cells that is a marker of previous cell divisions. Following cell division, a remnant of the midbody ring is retained by one cell (typically the older or "parent" cell) and persists through multiple cell divisions, such that multiple midbody remnants can accumulate in one cell. These remnants of the midbody ring, referred to herein as "midbody scars," can be used to identify and isolate dividing cells, e.g., progenitor or stem cells, in a population. This application relates to compositions and methods related to the newly discovered midbody scars.

In one aspect, the invention provides methods for detecting the presence of a midbody scar in a mammalian cell. The methods include contacting a mammalian cell suspected to have a midbody scar with an antibody or antigen-binding portion thereof that binds specifically to a polypeptide component of a midbody scar; and detecting binding of the antibody to its antigen, wherein binding of the antibody indicates the presence of a midbody scar in the mammalian cell.

In some embodiments, the methods include contacting the mammalian cell with two or more antibodies or antigen-binding portions thereof that each bind specifically to a polypeptide component of a midbody scar, and detecting binding of the two or more antibodies. Colocalized binding of the two or more of antibodies indicates the presence of a midbody scar.

In the methods described herein, the polypeptide component of the midbody scar can be, e.g., mitotic kinesin-like protein 1 (MKLP1); Epsilon tubulin (ϵ-tubulin); Centrosomal Protein 55 kDa (Cep55); and Aurora B kinase.

In some embodiments, the cell is in interphase, e.g., in G1, S, or G2 phase. Cells can be synchronized in interphase, e.g., in G1 (e.g., arrested by serum starvation), S (by thymidine block), or in G2 (by flow out of S phase). In some embodiments, the mammalian cell is a fixed cell, and/or a cell in a pathology specimen. The cell can be isolated cultured, or in tissue, e.g., in a fixed tissue sample. The cells or tissue can be from any organ in the human body, e.g., skin, heart, neural tissue, bone marrow, blood, liver, or lung, inter alia.

In another aspect, the invention provides methods for identifying a dividing cell in a population of mammalian cells, e.g., a population including both dividing cells and non-dividing cells. The methods include obtaining a population of mammalian cells comprising at least one cell suspected of being a dividing cell; and detecting a cell having one or more midbody scars; a cell having one or more midbody scars is a dividing cell. In some embodiments, the dividing cell is a cancerous cell. In some embodiments, the dividing cell is a stem or progenitor cell.

In some embodiments, the methods further include identifying cells having a desired number of midbody scars, e.g., 0 to 2 midbody scars per cell, or 4 or more midbody scars per cell. Once cells having the desired number of midbody scars have been identified, they can be selected, e.g., for isolation, characterization, ablation, or other further manipulation. For example, cells selected and isolated by a method described herein can be expanded in culture under conditions sufficient to provide a population of dividing cells, e.g., a population comprising a desired number of cells.

Identifying a cell with one or more midbody scars can be accomplished by optically detecting the presence of a cellular structure having morphological characteristics of a midbody scar, e.g., using phase contrast microscopy to analyze the cell. This analysis can be manual or automated. Alternatively or in addition, cells with one or more midbody scars can be identified by contacting the population of cells with a detectible antibody or antigen-binding portion thereof that binds specifically to a polypeptide component of a midbody scar; and detecting binding of the detectible antibody to the polypeptide; in this case, binding of the antibody indicates the presence of a midbody scar.

In some embodiments, the methods described herein use an antibody or antigen-binding portion thereof is bound or linked to a detectable moiety, and binding of the antibody to its antigen is detected by detecting the detectable moiety. The detectible antibody or antigen binding portion thereof can include, e.g., a fluorescent label, and identifying a cell with one or more midbody scars is can be achieved by detecting the presence of fluorescence from the detectible antibody or antigen binding portion thereof, e.g., using fluorescence microscopy, e.g., manually or using an automated system. In some embodiments, the detectible antibody includes or is linked to an enzyme, which when provided with an appropriate substrate produces a product that is detected.

In some embodiments, the population of cells is from a subject suspected of having a proliferative disorder, e.g., a pathology specimen, and the methods can be used to diagnose a proliferative disease in a subject. For example, the methods can include determining the percentage of cells in the sample that have a selected number of midbody scars; and comparing the percentage of cells in the sample to a reference percentage representing a sample from a subject that does not have a proliferative disorder; wherein the presence of a significantly higher number of dividing cells as compared to the reference sample indicates that the subject has a proliferative disorder.

In further aspects, the invention features methods of determining the presence of a midbody scar in an animal cell by contacting a cell suspected to have a midbody scar with an agent that binds specifically to a component of a midbody scar and detecting the agent, thereby determining the presence of the midbody scar. In some embodiments, the component of the midbody scar is MKLP1, ϵ-tubulin, Cep55, or Aurora B kinase. In some embodiments, the agent comprises a detectable moiety, e.g., a fluorescent label, or a radioactive isotope. The label also can be an enzyme, such as alkaline phosphatase or horseradish peroxidase, which when provided with an appropriate substrate produces a product that is detectible.

In some embodiments, the agent is an antibody that binds specifically to a midbody scar or midbody scar component. In some embodiments, the methods include determining the presence of a midbody scar using phase microscopy. In various embodiments, the components are either within cells or exposed on the surface of the cells.

In other aspects, the invention features methods of selecting a population of cells with one or more, e.g., a desired number of, midbody scars. In some embodiments, the methods include obtaining a population of cells wherein midbody scars are optionally labeled with a detectable moiety, detecting the midbody scars, and selecting cells with a desired number of midbody scars based on the presence or absence of the midbody scars, e.g., based on the presence of absence of the detectable moiety. In some embodiments, the methods include obtaining a population of cells and evaluating the cells using phase contrast microscopy, and selecting cells with a desired number of midbody scars based on the presence or absence of a cell structure having the morphological features of a midbody scar. In some embodiments, the desired number of midbody scars is 0, 1, 2, 3, 4, 5, 6, or 7 scars, e.g., between 0 and 2 or 4 or more scars. In some embodiments, the selection is done by an automated system.

In further aspects, the invention features methods of determining or estimating the replicative age (i.e., the number of times the cell has divided to form two progeny) of an animal cell by detecting midbody scars in an animal cell and counting the number of midbody scars per cell, wherein the number of midbody scars per cell indicates the number of divisions of the cell and thus the replicative age. In some embodiments, counting includes determining a level of a detectable entity per cell, e.g., a detectable entity bound covalently or non-covalently to a midbody scar or midbody scar component, e.g., an antibody to a midbody ring protein as described herein.

In other aspects, the invention features methods of identifying compounds that bind to a midbody scar (or component thereof) by providing a midbody scar, contacting the midbody scar with a test compound, and determining whether the compound binds to the midbody scar. In some embodiments, the midbody scar is isolated. In other embodiments, the midbody scar is on or in a cell. The cell can be in culture or in a tissue or tumor, e.g., in a pathology sample, e.g., including tissues known or suspected to include cells associated with a proliferative disorder. In some embodiments, determining whether the compound binds to the midbody scar includes determining whether the compound colocalizes with an agent described herein that binds to a midbody scar, e.g., an antibody that binds to a midbody ring protein as described herein.

In further aspects, the invention features methods of identifying compounds that bind to midbody scar components by providing a midbody scar component (e.g., MKLP1, $\epsilon$-tubulin, Cep55, or Aurora B kinase, or fragments thereof), contacting the midbody scar component with a test compound, and determining whether the test compound binds to the midbody scar component. In some embodiments, the midbody scar component is isolated, e.g., an isolated protein. In other embodiments, the midbody scar component is in a midbody scar, e.g., is part of an isolated midbody scar. In other embodiments, the midbody scar component is in a cell, e.g., is part of a midbody scar in a cell or in a tissue.

In other aspects, the invention features methods and compounds for targeting therapeutic or diagnostic compositions to cells that contain midbody scars. The methods include conjugating a therapeutic or diagnostic moiety to a compound that binds to a midbody scar on a cell to produce a therapeutic or diagnostic composition, and administering the therapeutic or diagnostic composition to a subject.

In some aspects, the invention features isolated midbody scars from mammalian cells and tissues, e.g., normal tissues, pathology tissues (e.g., known or suspected to include cancerous cells), and blood, e.g., from a mammal such as a human. The isolated midbody scars typically include certain proteins such as mitotic kinesin-like protein 1 (MKLP1), Epsilon Tubulin ($\epsilon$-tubulin), Cep55, and/or Aurora B kinase. In some embodiments, the midbody scars do not include $\gamma$-tubulin or centriolin. In some embodiments, the isolated midbody scars are from interphase cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

This patent and the corresponding application file contain at least one drawing executed in color. Copies of this patent or patent application publication with color drawing(s) will be provided by the Office upon request and payment of the necessary fee.

FIGS. 1A-1E are a series of micrographs depicting a mitotic kinesin-like protein 1 (MKLP1)-positive ring localized at the midbody during cytokinesis. FIG. 1A is a phase contrast picture. FIG. 1B depicts MKLP1 staining. FIG. 1C depicts $\gamma$-tubulin staining. FIG. 1D depicts DAPI staining of DNA. FIG. 1E is a merged combination of FIGS. 1B-1D, in which MKLP1 staining is pseudo-colored in red in the original, $\gamma$-tubulin staining is pseudo-colored in green in the original, and DAPI staining is pseudo-colored in blue in the original. The midbody structure is enlarged in the insets.

FIG. 2A is a phase contrast picture. FIG. 2B depicts MKLP1 staining. FIG. 2C depicts $\gamma$-tubulin staining. FIG. 2D depicts DAPI staining of DNA. FIG. 2E is a merged combination of FIGS. 2B-2D, in which MKLP1 staining is pseudo-colored in red in the original, $\gamma$-tubulin staining is pseudo-colored in green in the original, and DAPI staining is pseudo-colored in blue in the original. The midbody scar is enlarged in the insets.

FIGS. $3A_1$-$3C_5$ are a series of micrographs depicting a persistent midbody scar during mitosis. FIGS. $3A_1$-$3A_5$ depict metaphase. FIGS. $3B_1$-$3B_5$ depict anaphase. FIGS. $3C_1$-$3C_5$ depict telophase. FIGS. $3A_1$-$3B_1$, and $3C_1$ show phase contrast. FIGS. $3A_2$, $3B_2$, and $3C_2$ depict $\gamma$-tubulin staining. FIGS. $3A_3$, $3B_3$, and $3C_3$ depict MKLP1 staining. FIGS. $3A_4$, $3B_4$, and $3C_4$ depict DAPI staining of DNA. FIGS. $3A_5$, $3B_5$, and $3C_5$ depict a merged version of the three previous figures, with γ-tubulin pseudo-colored in green in the original, MKLP1 pseudo-colored in red in the original, and DAPI pseudo-colored in blue in the original. Midbody scar(s) can be observed at metaphase ($3A_3$; $3A_5$, red in the original), anaphase ($3B_3$; $3B_5$, red in the original), and telophase ($3C_3$; $3C_5$, red in the original). The midbody scars are enlarged in the insets.

Figure 4A:
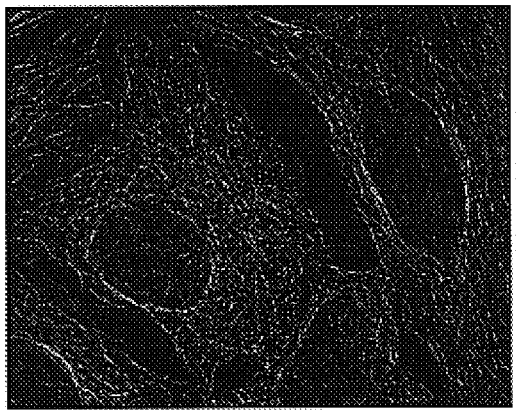
Figure 4B:
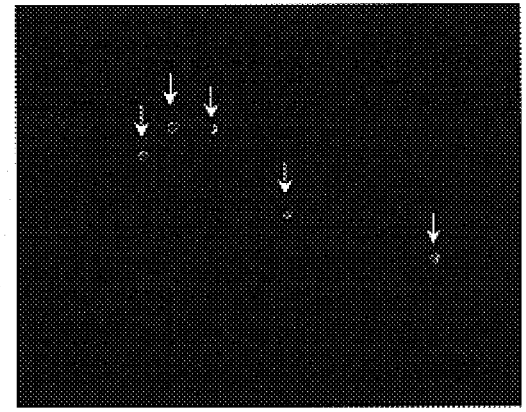
Figure 4C:
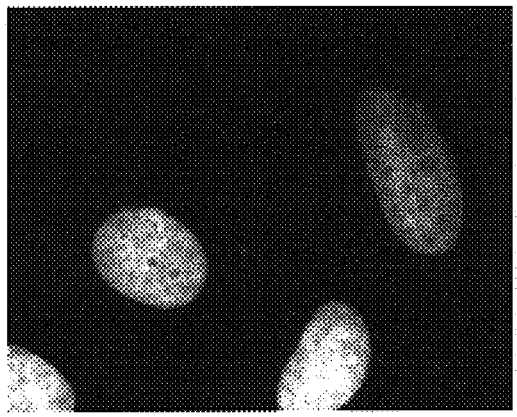
Figure 4D:

FIGS. 4A-4D are a series of fluorescence micrographs depicting a cell with multiple MKLP1-positive midbody scars. FIG. 4A depicts staining of α-tubulin. FIG. 4B depicts staining of MKLP1. FIG. 4C depicts DAPI staining of DNA. FIG. 4D is the merge of FIGS. 4A-4C, with α-tubulin pseudo-colored in green in the original, MKLP1 pseudo-colored in red in the original, and DAPI pseudo-colored in blue in the original. Four midbody scars are visible in one cell, and an adjacent cell contains one midbody scar.

Figure 5:
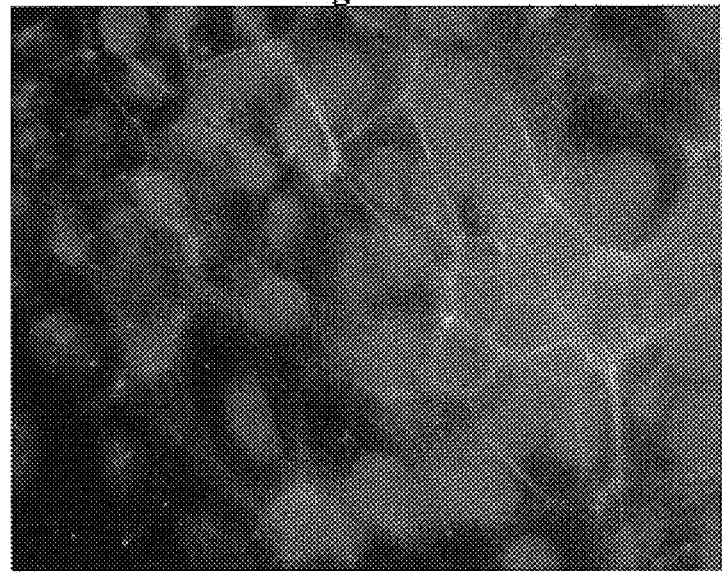

FIG. 5 is a photomicrograph of H9 human embryonic stem cells, with staining for nuclei and MKLP-1.

DETAILED DESCRIPTION

This invention includes compositions and methods related to a newly discovered cellular structure, the midbody scar. This structure is preferentially segregated to one cell during cytokinesis and persists through multiple cell divisions, such that a cell can accumulate multiple midbody scars, potentially accumulating one for each time it divides, e.g., as it "ages." These scars can also be used as markers to identify stem cells in a population (see below) and can be used to identify, isolate, and characterize various proliferating cells in human tissues and cell samples for use in numerous diagnostic and therapeutic methods.

Cytokinesis is a fundamental process that results in the division of a single cell with replicated chromosomes into two daughter cells with identical genetic composition (see, e.g., Glotzer, 2001, Annu. Rev. Cell Dev. Biol., 17:351-386; Glotzer, 2005, Science, 307:1735-1739; and Guertin, 2002, Microbiol. Mol. Biol. Rev., 66:155-178). During cytokinesis, a phase-dense material known as the midbody forms between the two daughter cells. This midbody has been shown to be involved in recruitment of secretory vesicles during daughter cell abscission (Gromley et al., 2005, Cell, 123:1-13).

Midbody Scars

This application describes the discovery of a new cellular structure related to the midbody. This structure, the midbody scar, can persist through several subsequent cell divisions, such that multiple midbody scars can be detected in some cells (Examples 1-4). As many as six midbody scars have been detected in a single cell, although the upper limit on number of midbody scars in a cell can be several times higher.

The midbody scars form when, following cytokinesis, the midbody is preferentially segregated to one of the resulting daughter cells. The other daughter cell receives no detectable trace of the midbody. As demonstrated herein, the midbody scar can segregate preferentially, possibly based on the existence of a previous scar in the cell. When a young cell with no midbody scar divides, the midbody scar may be segregated randomly. Importantly, when a stem or progenitor cell divides, e.g., a pluripotent or immortal cell, the midbody scar will generally segregate with the original stem cell, and not with the newly formed daughter cell, e.g., the cell that differentiates. Thus, the midbody scars are markers of stem and progenitor cells, and can be used to identify, target, and isolate these cells.

The midbody scar structure is localized adjacent to the plasma membrane, and is made up of several proteins, including those listed in Table 1. The midbody scar contains many of the proteins present in the midbody, with some exceptions; for example, in some embodiments, γ-tubulin, which is a component of the midbody, is not present in the midbody scar. The polypeptide components of midbody scars include kinases, other regulatory proteins, and structural proteins. The accumulation of midbody scar structures, including such regulatory proteins, may affect cell division processes.

TABLE 1

Exemplary Polypeptide Components of Mammalian Midbody Scars

| Protein name | EntrezGene database ID | Also known as |
| --- | --- | --- |
| mitotic kinesin-like protein 1 (MKLP1) | GeneID: 9493 | KIF-23; CHO1; KNSL5; and MKLP-1 |
| Epsilon tubulin (ε-tubulin) | GeneID: 51175 | TUBE1, TUBE; FLJ22589; and dJ142L7.2 |
| Centrosomal Protein 55 kDa (Cep55) | GeneID: 55165 | URCC6; C10orf3; and FLJ10540 |
| Aurora B kinase | GeneID: 9212 | AIK2; AIM1; ARK2; AurB; IPL1; STK5; AIM-1; and STK12 |

Isolation of Midbody Scars

Midbody scars are stable structures that can persist in cells through multiple cell cycles. Accordingly, the midbody scar structure can be isolated, in whole or in part, by common cell biology techniques. Methods of purification of proteins and protein complexes are known to one of skill in the art. The midbody scar can be purified under conditions suitable to keep the complex intact. For example, the membranes can be solubilized with a non-ionic detergent, such as Triton™ X-100 and the scars isolated on a density gradient and/or antibody affinity matrix. General methods of protein purification are described, e.g., in Scopes, *Protein Purification: Principles and Practice*, Springer (3d ed. 1993).

Methods of midbody purification are known (see, e.g., Kuriyama and Ensrud, 1999, Methods Cell Biol., 61:233-244; and Skop et al., 2004, Science, 305:61-66). These methods can be adapted for isolation of midbody scars. For example, Skop et al. (supra) describes the purification of midbodies from a synchronized population of mitotic cells. For example, the methods of Skop et al. (supra) can be used with interphase cells to obtain a preparation enriched in midbody scars. In some embodiments, a synchronized population of non-mitotic cells can be used to isolate midbody scars. In some embodiments, midbodies can be separated from midbody scars with a compound that binds specifically to a component of midbodies that is not found in midbody scars, e.g., γ-tubulin. Midbody scars can also be isolated or enriched further by the same method (e.g., using antibody-bound affinity purification beads or matrices, e.g., containing antibodies to a polypeptide component of the midbody scar as described herein).

Isolated midbody scars can be used to determine the identity of midbody scar or associated proteins. The protein complex can be dissociated by treatment with an ionic detergent, such as SDS, and the individual proteins can be isolated and identified, e.g., by mass spectrometry. Regulatory proteins, e.g., kinases, that are part of the midbody scar may be involved in cellular aging processes or in cell immortality (stem cells). Because the midbody scar is a remnant of the midbody, it is likely to contain many of the proteins present in the midbody (see, e.g., Skop et al., 2004, Science, 305:61-66). Additionally, there may be proteins present in the midbody scar that are not found in the midbody.

Detection of Midbody Scars

The midbody scars can be detected by a variety of methods. Midbody scars can be detected to determine a cell's replicative age, to select cell populations based on the presence of one or more midbody scars, to identify and/or target cells based on the presence of one or more midbody scars, and to study the characteristics of cells with midbody scars.

Midbody scars can be detected by using a molecule that binds to the midbody scar, e.g., an antibody that specifically binds to a midbody scar polypeptide or an antigenic fragment thereof, e.g., MKLP1, ϵ-tubulin, Cep55, or Aurora B kinase. A number of antibodies suitable for use in the methods described herein are known in the art and/or are commercially available. For example, anti-MKLP1 and anti-Aurora B antibodies are available from BD Biosciences (San Jose, Calif.) and Santa Cruz Biotechnology Inc. (Santa Cruz, Calif.). Antibodies to ϵ-tubulin are described in Chang and Stearns, Nature Cell Biology 2:30-35 (2000), and are available from Sigma-Aldrich (St. Louis, Mo.). Antibodies to Cep55 are described in Fabbro et al., Dev. Cell 9:477-488 (2005), and Zhao et al. Mol. Biol. Cell. 17:3881-3896 (2006), and are available from Abnova Corp. (Taipei City, Taiwan). The antibody can be, for example, an antigen-binding fragment of a full-length antibody. The antibody can also be a CDR-grafted antibody, diabody, triabody, minibody, humanized antibody, deimmunized antibody, or an antigen binding fragments thereof.

In some embodiments, the antibody is conjugated to a detectable entity, e.g., a fluorescent moiety, a radioactive isotope, an enzyme, a contrast agent, or a magnetic particle. In some embodiments, the antibody is not labeled with a detectable entity, but can itself be bound by a compound containing a detectable entity, e.g., an antibody to the compound or a member of a binding pair (e.g., avidin and biotin). When live cells are used, the midbody scar binding moiety or agent may be chosen to bind to an extracellular exposed portion of the midbody scar, e.g., a component of the scar that has some portion that is exposed on the surface of the cell. Alternately, the midbody scar binding moiety or agent can be designed to cross the cell membrane to bind to a portion of the midbody scar not exposed extracellularly (i.e., an intracellular portion). For example, an antibody (or other binding agent) that binds to an intracellular portion of the midbody scar can include a cell internalization peptide, such as Antennapedia, HIV-derived TAT peptide, penetratins, transportans, or hCT derived cell-penetrating peptides, see, e.g., Caron et al., (2001) Mol Ther. 3(3):310-8; Langel, *Cell-Penetrating Peptides: Processes and Applications* (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49, or can be packaged inside a carrier that allows the antibody to cross the membrane, e.g., a vesicle or liposome.

In other embodiments, a polypeptide that is a component of the midbody scar can be produced as a fusion protein that includes a fluorescent polypeptide, such as GFP. Such fluorescent fusion proteins can be chosen such that the midbody scar polypeptide still functions in the midbody scar complex. Such fusion proteins can be introduced into cells and used to mark midbody scars, study them in living cells, and isolate them based on the presence of the fluorescence marker.

Detection of midbody scars in a cell allows the determination of the replicative age of the cell. As a cell divides, it can accumulate a midbody scar with each cell cycle, therefore, cells with higher numbers of midbody scars are those that have undergone a higher number of cell divisions compared with cells having fewer or lacking scars.

In some embodiments, the relative number of midbody scars can be approximated by the relative level of signal, e.g., a fluorescent signal (e.g., from MKLP1-GFP or a fluorescently labeled antibody to a midbody scar protein), in the cells. In this system, interphase cells with two midbody scars will have approximately twice the signal as interphase cells with one midbody scar. Based on the relative level of signal, the cells can be sorted using routine methods to select a population that is enriched for the presence of midbody scars, e.g., for a specific number or range of numbers of midbody scars. Isolation of a homogeneous population of cells (e.g., all dividing cells, e.g., all stem or progenitor cells) can be useful, e.g., for achieving a standardized response to drugs or other cell stimuli, or for preparing a population of stem cells for use in other applications, e.g., therapeutic or diagnostic applications as described herein.

Stem Cells

Stem cells are primal cells that, upon division, can give rise both to another stem cell and a cell that will differentiate and ultimately die (see, e.g., Zipori, Nat. Rev. Genet. 5:873-878 (2004)). Totipotent stem cells are produced from the fusion of an egg and sperm cell. Cells produced by the first few divisions of the fertilized egg cell are also totipotent. These cells can differentiate into embryonic and extraembryonic cell types. Pluripotent stem cells are the descendants of totipotent cells and can differentiate into cells derived from the three germ layers. Multipotent stem cells can produce only cells of a closely related family of cells (e.g. hematopoietic stem cells differentiate into red blood cells, white blood cells, or platelets). Unipotent cells can produce only one cell type, but have the property of self-renewal, which distinguishes them from non-stem cells. Stem cells are now believed to be present, though extremely scarce, in most tissues of the mammalian body, including the adult body.

Presently, there are no good universal markers for stem cells. CD44 is a widely used marker, but does not detect all stem cell populations. It is reasonable to believe that midbody scars are present in all stem cell populations and can therefore be used as a universal stem cell marker. Therefore, midbody scars can be used to identify stem cells prospectively, thereby potentially avoiding the otherwise necessary tasks of growing cells, cloning cells, and passing cells through mice to identify stem cell populations. The use of midbody scars as a marker allows the identification of stem cells in various organs and environments.

An emerging cancer stem cell theory posits that cancer develops from stem cells rather than from de-differentiated cells as previously believed (see, e.g., Marx, Science 301: 1308-1310 (2003); Bell and Van Zant, Oncogene 23:7290-7296 (2004); Jordan et al., N. Eng. J. Med. 355:1253 (2006)). This new theory has gained considerable acceptance. Such stem cells should have midbody scars that would serve as markers for tumor stem cells. These structures could also serve as targets for tumor cell killing. Moreover, isolated midbody scars could be characterized to identify novel markers for therapeutic targets.

Identification and Selection of Dividing Cells

Dividing cells, such as stem cells and cancer cells, can be identified by the presence and/or number of midbody scars accumulated during or after each division cycle. Thus, midbody scars can be detected to select a population of cells that are dividing. For example, cells can be selected that have relatively few (e.g., 0 to 2) midbody scars or that have relatively many (e.g., 4 or more) midbody scars. This selection can be performed manually, or can be automated, e.g., by flow cytometry cell sorting, e.g., fluorescence activated cell sorting (FACS) for cells with midbody scars that are labeled with fluorescent moieties or magnetic activated cell sorting (MACS) for cells with midbody scars that are labeled with magnetic beads; or optical image-based cell sorting, based on the detection of cellular structures with the morphological features of midbody rings, e.g., using phase contrast microscopy. At high magnification (i.e., over about 60×-100×), small bright rings of about 2 μm are visible.

Once the cells have been identified, the cells can be selected either with a pick-to-remove (i.e., select the cells that lack midbody scars for removal, and remove them, e.g., by aspiration with culture media or by laser ablation using standard methods) or a pick-to-keep (i.e., select the cells that have a selected number of midbody scars and move them to a new culture vessel) scheme. Dividing cells such as stem or progenitor cells can be maintained in culture using methods known in the art, e.g., including the use of specialized stem cell culture media including the BMP antagonist noggin and basic fibroblast growth factor (bFGF) and/or feeder cells such as primary or immortalized mouse embryonic fibroblasts (MEFs). See, for example, Xu et al., Nat. Meth. 2(3):185-190 (2005), U.S. Pat. No. 7,005,252, and the protocols of the WiCell Research Institute, Inc., available on the world wide web at WiCell.org. When passaging the cells or otherwise treating the cells to release them from a culture substrate, it is desirable to use a method that is not destructive of extracellular proteins; thus, the use of Accutase™ (a gently enzyme cell detachment medium, from Innovative Cell Technologies, Inc.), or removal/reduction in levels of divalent cations using chelators such as EGTA or EDTA, is preferred over the use of strong proteases such as trypsin, which can disrupt the midbody scars both outside and inside cells.

As one example, a population of cells can be diluted and plated into a multiwell plate or other suitable vessel in such a manner that only one or a small number of cells is plated in each well. The wells can be evaluated, e.g., manually or by automated means, for the presence of cells with one or more, e.g., a selected number of, midbody scars. Those wells having cells with midbody scars can be selected for clonal expansion, and cultured using methods known in the art. For example, a clonal population of stem cells can be produced using a method described herein and culture methods known in the art for the maintenance and propagation of stem cells.

Screening Methods

The invention provides methods for identifying compounds, e.g., small organic or inorganic molecules (e.g., those with a molecular weight of less than 1,000 Da), oligopeptides, oligonucleotides, or carbohydrates, capable of binding to midbody scars or midbody scar polypeptides. Such compounds can be useful in methods relating to studying and/or altering aging and longevity.

In certain embodiments, screening methods of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 100,000 grams per mole, less than about 50,000 grams per mole, less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include proteins, peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp. (San Diego, Calif.). Libraries can be designed to cover a diverse range of compounds. For example, a library can include 500, 1000, 10,000, 50,000, 100,000, or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., Gordon et al., J. Med. Chem. (1994) 37:1385-1401; DeWitt and Czamik, Acc. Chem. Res. (1996) 29:114; Armstrong et al., Acc. Chem. Res. (1996) 29:123; Ellman, Acc. Chem. Res. (1996) 29:132; Gordon et al., Acc. Chem. Res. (1996) 29:144; Lowe, Chem. Soc. Rev. (1995) 309; Blondelle et al., Trends Anal. Chem. (1995) 14:83; Chen et al., J. Am. Chem. Soc. (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds can be prepared according to a variety of methods known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., Bodansky "Principles of Peptide Synthesis", 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained.

The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of DeWitt et al., (Proc. Natl. Acad. Sci. USA, 90:6909-13 (1993)). Other synthesis methods, including the "tea-bag" technique of Houghten (see, e.g., Houghten et al., Nature, 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., J. Med. Chem., supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described herein.

The invention provides methods for identifying compounds capable of binding to midbody scars or midbody scar polypeptides (e.g., MKLP1 or Aurora B kinase).

In some embodiments, the assay is a cell-based assay in which a cell that includes at least one midbody scar is contacted with a test compound, and the ability of the test compound to bind to the midbody scar is determined, e.g., by binding and localization to the midbody scar. The cell, for example, can be of mammalian origin, e.g., murine, rat, or human origin.

The ability of a compound to interact with a midbody scar or midbody scar polypeptide with or without the labeling of any of the interactants can be evaluated. For example, a microphysiometer can be used to detect the interaction of a compound with a midbody scar or midbody scar polypeptide without labeling either the compound or the midbody scar or midbody scar polypeptide (McConnell et al., 1992, Science, 257:1906-1912). As used herein, a "microphysiometer" (e.g., Cytosensor®) is an analytical instrument that measures the rate at which a cell acidifies its environment using a light-addressable potentiometric sensor (LAPS). Changes in this acidification rate can be used as an indicator of the interaction between a compound and a midbody scar or midbody scar polypeptide.

Soluble and/or membrane-bound forms of midbody scars and midbody scar polypeptides can be used in cell-free assays as described herein. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of isolated midbody scars and one or more test compounds under conditions and for a time sufficient to allow the two components to interact and bind, thus forming a complex that can be removed and/or detected.

The interaction between two molecules can also be detected, e.g., using fluorescence resonance energy transfer (FRET) (see, for example, Lakowicz et al., U.S. Pat. No. 5,631,169 and Stavrianopoulos et al., U.S. Pat. No. 4,868,103). A fluorophore label on the first 'donor' molecule is selected such that its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter).

In another embodiment, determining the ability of a midbody scar or midbody scar polypeptide to bind to a target molecule can be accomplished using real-time Biomolecular Interaction Analysis (BIA) (e.g., Sjolander et al., 1991, Anal. Chem., 63:2338-2345 and Szabo et al., 1995, Curr. Opin. Struct. Biol., 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target midbody scar, or midbody scar polypeptide, or the test substance is anchored onto a solid phase. The target midbody scar or midbody scar polypeptide/test compound complexes anchored on the solid phase can be detected at the end of the reaction. The target midbody scar or midbody scar polypeptide can be anchored onto a solid surface, and the test compound, which is not anchored, can be labeled, either directly or indirectly, with detectable labels discussed herein.

Binding compounds are screened by identifying from a group of test compounds those that bind to a midbody scar or midbody scar polypeptide. Binding of a test compound to a midbody scar or midbody scar polypeptide can be detected, for example, in vitro by reversibly or irreversibly immobilizing the test compound(s) on a substrate, e.g., the surface of a well of a 96-well polystyrene microtiter plate. Methods for immobilizing polypeptides and other small molecules are well known in the art. For example, microtiter plates can be coated with midbody scars or a midbody scar polypeptide by adding the midbody scar polypeptide in a solution (typically, at a concentration of 0.05 to 1 mg/ml in a volume of 1-100 µl water or buffer) to each well, and incubating the plates at room temperature to 37° C. for a given amount of time, e.g., for 0.1 to 36 hours. Polypeptides not bound to the plate can be removed, e.g., by pouring excess solution from the plate, and then washing the plate (once or repeatedly) with water or a buffer. The plate can then be washed with a buffer that lacks the bound polypeptide.

To block the free protein-binding sites on the plates, plates can be blocked with a protein that is unrelated to the bound polypeptide. For example, 300 µl of bovine serum albumin (BSA) at a concentration of 2 mg/ml in Tris-HCl can be used. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded Sepharose®, can be used as the substrate. Test compounds can then be added to the coated plate and allowed to bind to the midbody scar or midbody scar polypeptide (e.g., at 37° C. for 0.5-12 hours). The plate can then be washed as described above.

Binding of a midbody scar or midbody scar polypeptide to a second compound, e.g., a test compound described above, can be detected by any of a variety of art-known methods. For example, an antibody that specifically binds to a midbody scar polypeptide (e.g., an anti-MKLP1 or Aurora B kinase antibody) can be used in an immunoassay. If desired, the antibody can be labeled (e.g., fluorescently or with a radioisotope) and detected directly (see, e.g., West and McMahon, J. Cell Biol., 74:264, (1977)). Alternatively, a second antibody can be used for detection (e.g., a labeled antibody that binds to the Fc portion of the anti-midbody scar polypeptide antibody).

In an alternative detection method, the midbody scar or midbody scar polypeptide is labeled (e.g., with a radioisotope, fluorophore, chromophore, or the like), and the label is detected. In still another method, a midbody scar polypeptide is produced as a fusion protein with a protein that can be detected optically, e.g., green fluorescent protein (which can be detected using an appropriate light source). In an alternative method, the polypeptide is produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen, which can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various methods for identifying polypeptides, e.g., test polypeptides, that bind to a midbody scar polypeptide, the conventional two-hybrid assays of protein/protein interactions can be used (see e.g., Chien et al., Proc. Natl. Acad. Sci. USA, 88:9578 (1991); Fields et al., U.S. Pat. No. 5,283,173; Fields and Song, Nature, 340:245 (1989); Le Douarin et al., Nucleic Acids Research, 23:876 (1995); Vidal et al., Proc. Natl. Acad. Sci. USA, 93:10315-10320 (1996); and White, Proc. Natl. Acad. Sci. USA, 93:10001-10003 (1996)). Typically, two-hybrid methods involve reconstitution of two separable domains of a transcription factor. One fusion protein contains the midbody scar polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the midbody scar polypeptide to the test polypeptide reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

Additionally, polypeptides involved in the removal or degradation of midbody scars can be identified.

Antibodies

Full length proteins or polypeptides of the midbody scar, or immunogenic fragments or analogs thereof, can be used to raise antibodies useful in the methods described herein; such polypeptides can be produced by recombinant techniques or synthesized (see, for example, Stewart, "Solid Phase Peptide Synthesis," Freeman (1968); Sambrook et al., *Molecular Cloning: A Laboratory Manual*, Cold Spring Laboratory, Cold Spring Harbor, N.Y. (1989); Ausubel et al. (Eds.), *Current Protocols in—Molecular Biology*, John Wiley & Sons, New York, N.Y., 1999 and preceding editions; and U.S. Pat. No. 4,237,224). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a polypeptide of the invention. Host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies are heterogeneous populations of antibody molecules that are contained in the sera of the immunized animals.

Antibodies for use in the new methods include polyclonal antibodies and, in addition, monoclonal antibodies, humanized or chimeric antibodies, single chain antibodies, Fab fragments, F(ab')$_2$ fragments, CDR-grafted antibodies, deimmunized antibodies, molecules produced using a Fab expression library, and antigen binding fragments thereof Monoclonal antibodies (mAbs), which are homogeneous populations of antibodies to a particular antigen, can be prepared using the polypeptides of the invention described above and standard hybridoma technology (see, for example, Kohler et al., Nature, 256:495, 1975; Kohler et al., Eur. J. Immunol., 6:511, 1976; Kohler et al., Eur. J. Immunol., 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al. (*Nature*, 256:495, 1975, and U.S. Pat. No. 4,376,110); the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., "Monoclonal Antibodies and Cancer Therapy," Alan R. Liss, Inc., pp. 77-96, 1983). Such antibodies can be of any immunoglobulin class including IgG, IgM, IgE, IgA, IgD and any subclass thereof. Hybridomas producing mAbs may be cultivated in vitro or in vivo. The ability to produce high titers of mAbs in vivo makes this a particularly useful method of production.

Once produced, polyclonal or monoclonal antibodies are tested for specific recognition of midbody scar polypeptides, or fragment thereof, by Western blot or immunoprecipitation analysis by standard methods (e.g., as described in Ausubel et al., supra). Antibodies that specifically recognize and bind to midbody scar proteins, or fragments thereof, are useful in the methods described herein. For example, such antibodies can be used in an immunoassay to monitor a midbody scar protein, or fragment thereof, in mammalian cells (for example, to determine the amount or subcellular location of a midbody scar protein, or fragment thereof).

In some embodiments, antibodies are produced using fragments of the midbody scar polypeptides that lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

In other embodiments, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Generally, partially human antibodies and fully human antibodies have a longer half-life within the human body than other antibodies. Accordingly, lower dosages and less frequent administration are often possible than with non-human antibodies. Modifications such as lipidation can be used to stabilize antibodies and to enhance uptake and tissue penetration (e.g., into the brain). A method for lipidation of antibodies is described by Cruikshank et al. (J. Acquir. Immune Defic. Syndr., 14:193, 1997).

Alternatively, techniques described for the production of single chain antibodies (U.S. Pat. Nos. 4,946,778, 4,946,778, and 4,704,692) can be adapted to produce single chain antibodies against midbody scar proteins, or fragments thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed (Huse et al., Science, 246:1275, 1989) to allow rapid and easy identification of monoclonal Fab fragments with the desired specificity.

Antibodies to midbody scar polypeptides can, in turn, be used to generate anti-idiotype antibodies using techniques well known to those skilled in the art (see, e.g., Greenspan et al., FASEB J., 7:437, 1993; Nissinoff, J. Immunol., 147:2429, 1991). For example, antibodies that bind to a midbody scar polypeptide and competitively inhibit the binding of a binding partner of that midbody scar polypeptide can be used to generate anti-idiotypes that resemble a binding partner binding domain of the protein and, therefore, bind and neutralize a binding partner of the protein. Such neutralizing anti-idiotypic antibodies or Fab fragments of such anti-idiotypic antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics, 7:13-21, 1994; see also U.S. Pat. Nos. 5,545,806 and 5,569,825).

Therapeutic and Diagnostic Uses

Antibodies to midbody scar proteins can be used in therapeutic or diagnostic methods as described herein, e.g., to target therapeutics or diagnostic moieties to a subpopulation of cells with midbody scars. Identification of cells having midbody scars can also enable the targeting of other therapeutic modalities, e.g., laser ablation based on the presence of midbody scars to remove hyperproliferating stem cells from tissues such as tumors, or skin lesions such as psoriatic lesions, and thereby treat proliferative disease.

For example, the detection of midbody scars can be used to detect proliferating cells in a sample suspected of containing cancerous tissues. In some embodiments, the cells in the sample are fixed and contacted with one or more antibodies to a polypeptide component of a midbody scar. One of skill in the art would be able to determine whether the dividing cells, i.e., cells with a number of midbody scars, are cancerous cells. For example, the percentage of dividing cells in the sample could be compared to a reference sample that represents the percentage of dividing cells in a normal sample. Alternatively, other indicia, such as morphology or the presence of cancer markers, can also be used to confirm a diagnosis of a proliferative disorder.

Midbody scars can also be used to isolate proliferating cells, e.g., stem or progenitor cells, and grow them for a multitude of clinical applications including reversing, delaying the progression of, or preventing degenerative diseases such as Alzheimer's and Parkinson's diseases, repairing damaged cardiac tissue after an ischemic injury, e.g., after a myocardial infarction, to provide dermal and epidermal progenitor cells to regrow skin in subjects who are in need thereof, e.g., subjects with severe burns, and to target proliferating cells, e.g., cancer cells. Midbody scars can also be used for the characterization of such cells.

Alternatively, antibodies to components of the midbody scar can be used to target toxins (e.g., proteins, radioactive molecules) to kill highly proliferative cells, e.g., cancer or psoriasis cells, by linking toxins to antibodies to extracellular components of the midbody scars, or a dye or other label that can be bound to the cells that contain the scars and then selectively heated/killed, e.g., by lasers tuned to the particular absorption wavelength of the dye or label.

The methods described herein in which antibodies to midbody scar polypeptides are employed may be performed, for example, by utilizing pre-packaged diagnostic kits comprising at least one such specific antibody described herein, which may be conveniently used, for example, in clinical settings, to diagnose subjects exhibiting symptoms of disorders associated with aberrant expression of nucleic acids or polypeptides.

In some aspects, a compound (e.g., an antibody or antigen-binding fragment thereof) that binds to a midbody scar on a cell can be used in the production of a composition, e.g., a therapeutic or diagnostic composition, by conjugating a therapeutic or diagnostic moiety such as a drug, toxin, chelator, a boron compound and a detectable label, to the midbody-scar binding compound. Methods for making such compositions are known in the art, see, e.g., McCarron et al., Mol Interv. 5(6):368-80 (2005), and U.S. Pat. Pub. No. 2006/0088539. The compositions can be used to target drug molecules to cells that contain midbody scars. In some embodiments, these compositions can be used to treat disorders associated with cellular proliferation. Examples of cellular proliferative disorders include atherosclerosis, rheumatoid arthritis, idiopathic pulmonary fibrosis, scleroderma, cirrhosis of the liver, lupus, vasculitis, endometriosis, uterine fibroids, prostatic hyperplasia, nephritis, skin disorders, e.g., psoriasis, and cancer, e.g., carcinoma, sarcoma, metastatic disorders, or hematopoietic neoplastic disorders, e.g., leukemias. Specific cancers can include prostate, breast, and ovarian cancers. In other embodiments, these compositions can be used to target diagnostic moieties to cells in vitro or in vivo that contain midbody scars.

For example, the drug moiety can be a protein or polypeptide possessing a desired biological activity. Such proteins include, for example, toxins such as abrin, ricin A, maytansinoids, *Pseudomonas* exotoxin, or *Diphtheria* toxin; proteins such as tumor necrosis factor, alpha-interferon, beta-interferon, nerve growth factor, platelet derived growth factor, tissue plasminogen activator; and biological response modifiers such as lymphokines, interleukin-1, interleukin-2, interleukin-6, granulocyte macrophage colony stimulating factor, granulocyte colony stimulating factor, or other growth factors. Conjugated antibodies can be used to target drug molecules to cells that contain midbody scars. In one aspect, these antibodies can be used to treat disorders associated with cellular proliferation, e.g., cancers or psoriasis.

Techniques for conjugating a therapeutic or diagnostic moiety to an antibody are well known (see, e.g., Arnon et al., 1985, "Monoclonal Antibodies For Immunotargeting Of Drugs In Cancer Therapy", in Monoclonal Antibodies And Cancer Therapy, Reisfeld et al., Eds., Alan R. Liss, Inc. pp. 243-256; Hellstrom et al., 1987, "Antibodies For Drug Delivery", in Controlled Drug Delivery, 2nd ed., Robinson et al., Eds., Marcel Dekker, Inc., pp. 623-653; Thorpe, 1985, "Antibody Carriers Of Cytotoxic Agents In Cancer Therapy: A Review", in Monoclonal Antibodies '84: Biological And Clinical Applications, Pinchera et al., Eds., pp. 475-506; "Analysis, Results, And Future Prospective Of The Therapeutic Use Of Radiolabeled Antibody In Cancer Therapy", in Monoclonal Antibodies For Cancer Detection And Therapy, Baldwin et al., Eds., Academic Press, pp. 303-316, 1985; and Thorpe et al., 1982, Immunol. Rev., 62:119-158). Alternatively, an antibody can be conjugated to a second antibody to form an antibody heteroconjugate as described by Segal in U.S. Pat. No. 4,676,980.

Pharmaceutical Formulations

Once a candidate compound that binds to a midbody scar has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al., J. Antibiot., 41:1430-8 (1988). Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

The compounds and agents, nucleic acids, polypeptides, and antibodies (all of which can be referred to herein as "active compounds"), can be incorporated into pharmaceutical compositions. Such compositions typically include the active compound and a pharmaceutically acceptable carrier or excipient. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

There are a number of methods by which the new compositions for use in the new methods can be delivered to subjects, in general, and to specific cells or tissue in those subjects, in particular. In one example, plasmids encoding antibodies specific to midbody scar components (e.g., intrabodies) can be injected into a tissue. The plasmids would then enter cells in that tissue and express a specific antibody, which, in turn, would bind to the targeted midbody scar protein. Delivery specificity of such plasmids can be enhanced by associating them with organ- or tissue-specific affinity, so that they preferentially enter specified cell types.

Compounds and their physiologically acceptable salts and solvates may be formulated for administration by inhalation or insufflation (either through the mouth or the nose) or oral, buccal, parenteral or rectal administration.

The compounds will generally be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use. Where the compositions are intended for use in a specific treatment area, e.g., for treating a tumor or psoriatic lesion, the compositions can be administered by one or more local injections into the tumor site to diminish as much as possible any side effects relating to the compound's activities outside of the treatment area.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Methods for making such formulations are well known and can be found in, for example, Remington: The Science and Practice of Pharmacy, University of the Sciences in Philadelphia (USIP), 2005.

The compositions can also be formulated for intracellular delivery of the active compounds, using methods known in the art. For example, the compositions can include liposomes or other carriers that deliver the active compound across the plasma membrane. Vesicles that are covered with membrane-permeant peptides, such as Tat or Antennapedia, can also be used. A number of other methods for enhancing intracellular delivery are familiar to those of skill in the art.

It is recognized that the pharmaceutical compositions and methods described herein can be used independently or in combination with one another. That is, subjects can be administered one or more of the pharmaceutical compositions, e.g., pharmaceutical compositions comprising a nucleic acid molecule or protein of the invention or a modulator thereof, subjected to one or more of the therapeutic methods described herein, or both, in temporally overlapping or non-overlapping regimens. When therapies overlap temporally, the therapies may generally occur in any order and can be simultaneous (e.g., administered simultaneously together in a composite composition or simultaneously but as separate compositions) or interspersed. By way of example, a subject afflicted with a disorder described herein can be simultaneously or sequentially administered both a cytotoxic agent which selectively kills aberrant cells and an antibody (e.g., an antibody of the invention) which can, in one embodiment, be conjugated or linked with a therapeutic agent, a cytotoxic agent, an imaging agent, or the like.

EXAMPLES

Example 1

An MKLP 1-Positive Ring Localizes at the Midbody During Cytokinesis

During cytokinesis, a phase-dense material known as the midbody forms between the two daughter cells (FIG. 1A).

Diploid, telomerase-immortalized human RPE cells (hTERT-RPE-1s, Clontech Laboratories, Inc.; Morales et al., 1999, Nat. Genet., 21:115-118) and HeLa cells (American Type Culture Collection) were used in the experiments described herein. All cells were grown using standard methods, see, e.g., Gromley et al., 2003, J. Cell Biol., 161:535-545. HeLa cells were transfected as previously described (using Lipofectamine™ transfection reagent, Invitrogen). Cells undergoing cytokinesis were fixed and stained simultaneously with antibodies to MKLP1 and γ-tubulin, as well as 4'-6-Diamidino-2-phenylindole (DAPI), using standard methodology.

Antibodies to the following proteins were used in the Examples described herein: α-tubulin and γ-tubulin (Sigma-Aldrich); Aurora B (Transduction Laboratories); MKLP-1 (Santa Cruz Biotechnology, Inc.); and GT335 for stabilized microtubules (Gromley et al., 2003, J. Cell Biol., 161:535-545).

Cells were prepared for immunofluorescence, imaged, and deconvolved (Metamorph, Universal Imaging Corp.) using either formaldehyde, formaldehyde followed by methanol, or methanol alone as previously described (Dictenberg et al., 1998, J. Cell Biol., 141:163-174). All immunofluorescence images are two-dimensional projections of three-dimensional images to ensure that all stained material was visible in two-dimensional images. Quantification of signals produced by immunofluorescence staining for various midbody antigens was performed as described for centrosome protein quantification (Gromley et al., 2003, J. Cell Biol., 161:535-545).

A ring of MKLP1 staining colocalized with the midbody structure, along with γ-tubulin (FIGS. 1B-1E). FIG. 1B depicts MKLP1 staining as a ring structure associated with the midbody. FIG. 1C depicts γ-tubulin staining, also as a ring structure associated with the midbody. FIG. 1D depicts DAPI staining of DNA. FIG. 1E is a merged combination of FIGS. 1B-1D, in which MKLP1 staining is pseudo-colored in red, γ-tubulin staining is pseudo-colored in green, and DAPI staining is pseudo-colored in blue.

These results confirm the presence of MKLP1 that localizes at the midbody during cytokinesis, and demonstrate the presence of a ring structure therein.

Example 2

A Midbody Scar Persists in Prophase Cells

Figure 2A:
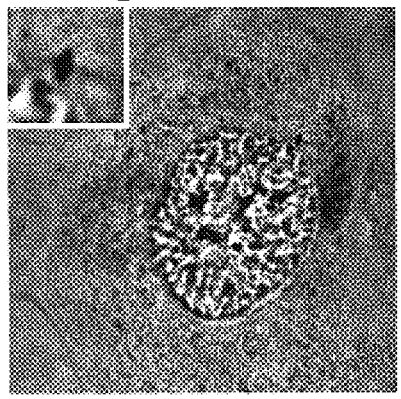
FIGS. 2A-2E are a series of micrographs depicting a persistent midbody scar in a prophase cell.
Figure 2B:
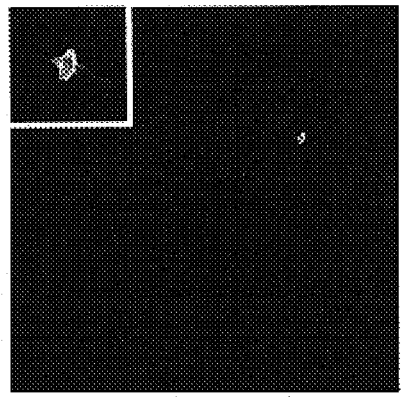
Figure 2C:
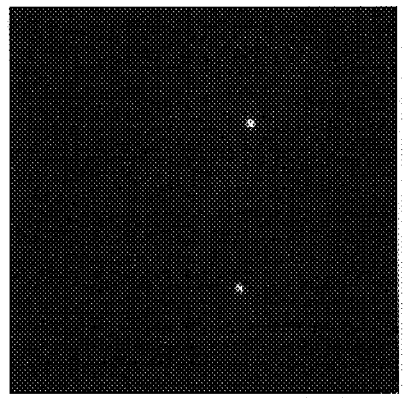
Figure 2D:
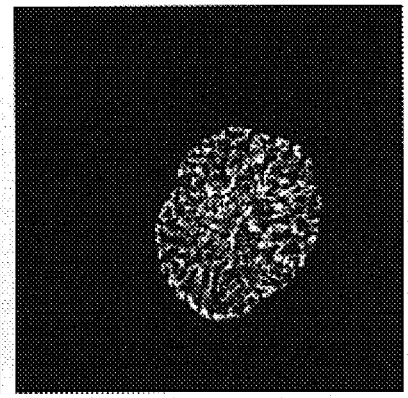
Figure 2E:
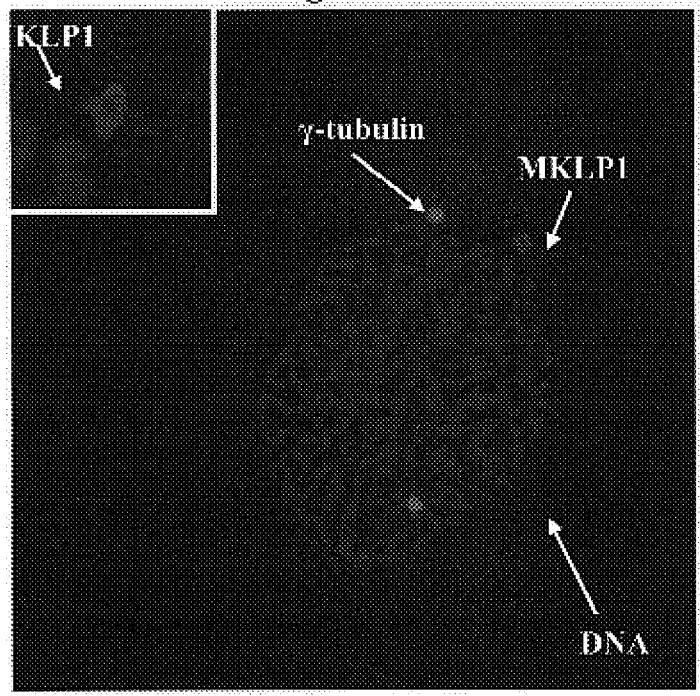

A phase-dense midbody-like structure was observed in a prophase cell (FIG. 2A). This structure is likely to be the remnants of the midbody ring from a previous mitosis, referred to herein as a midbody scar. A prophase cell was fixed and stained simultaneously with antibodies to MKLP1 and γ-tubulin, as well as DAPI. FIG. 2B depicts MKLP1 staining. FIG. 2C depicts γ-tubulin staining. FIG. 2D depicts DAPI staining of DNA. FIG. 2E is a merged combination of FIGS. 2B-2D, in which MKLP1 staining is pseudo-colored in red in the original, γ-tubulin staining is pseudo-colored in green in the original, and DAPI staining is pseudo-colored in blue in the original. The midbody scar is enlarged in the insets. The midbody scar contained at least MKLP1 (FIGS. 2B and 2E) and Aurora B kinase, but lacked α-tubulin and γ-tubulin (FIGS. 2C and 2E). This example demonstrates that a midbody-like structure containing MKLP1 and Aurora B kinase can be found in prophase cells.

Example 3

The Midbody Scar Persists During Mitosis

Cells in various stages of mitosis were fixed and stained to visualize MKLP1, γ-tubulin, and DNA (FIGS. $3A_1$-$3C_5$). FIGS. $3A_1$-$3A_5$ depict metaphase. FIGS. $3B_1$-$3B_5$ depict anaphase. FIGS. $3C_1$-$3C_5$ depict telophase. FIGS. $3A_1$, $3B_1$, and $3C_1$ show phase contrast. FIGS. $3A_2$, $3B_2$, and $3C_2$ depict γ-tubulin staining. FIGS. $3A_3$, $3B_3$, and $3C_3$ depict MKLP1 staining. FIGS. $3A_4$, $3B_4$, and $3C_4$ depict DAPI staining of DNA. FIGS. $3A_5$, $3B_5$, and $3C_5$ depict the merge of the three previous figures, with γ-tubulin pseudo-colored in green in the original, MKLP1 pseudo-colored in red in the original, and DAPI pseudo-colored in blue in the original. Midbody scars were found in mitotic cells at all stages of mitosis, including prometaphase, metaphase (FIGS. $3A_3$ and $3A_5$), anaphase (FIGS. $3B_3$ and $3B_5$), and telophase (FIGS. $3C_3$ and $3C_5$). Additionally, the midbody scar was still observed when MKLP1 localized to mitotic spindles. These findings indicate that the midbody scar is a persistent structure that is maintained through mitosis.

Example 4

Accumulation of Midbody Scars

Cells were also found to accumulate multiple midbody scars from multiple cell divisions. Interphase cells were fixed and stained to visualize MKLP1, α-tubulin, and DNA. FIG. 4A depicts staining of α-tubulin. FIG. 4B depicts staining of MKLP1. FIG. 4C depicts DAPI staining of DNA. FIG. 4D is the merge of FIGS. 4A-4C, with α-tubulin pseudo-colored in green in the original, MKLP1 pseudo-colored in red in the original, and DAPI pseudo-colored in blue in the original. FIGS. 4A-4D show an interphase cell that contains four visible midbody scars. This demonstrates that after multiple round of mitosis, midbody scars can be accumulated in cells. At the end of cytokinesis, the midbody was found to retract preferentially to one of the daughter cells.

Example 5

Segregation of Midbody Scars is Nonrandom in Tumor Cells and Embryonic Stem Cells During mitosis, if segregation of midbody scars was random, they would be expected to be distributed equally between the two daughter cells.

Therefore, segregation of midbody scars was evaluated in human HeLa cervical cancer cells and human H9 embryonic stem cells cultured by standard methods, see, e.g., U.S. Pat. No. 7,005,252, using the immunofluorescence and microscopy methods described herein.

Nonrandom (polarized) accumulation of midbody scars was observed in HeLa tumor cells. In a sample of 145 cells in telophase, 40 (28%) showed equal distribution of the midbody scars to the daughter cells, while 105 (72%) showed distribution to one cell. In telophase cells with 3 or 4 scars, 67-72% show asymmetric inheritance (3,0 or 4,0) (n=1,234 telophase cells counted). In another sample, 44% of the HeLa cells had 1-3 rings/cell (n=4,678).

An even more marked non-random distribution pattern was observed in the H9 embryonic stem cells (shown in FIG. 5). In a population of undifferentiated stem cells, 88% had 1-7 rings/cell (n=1,256), whereas 9% of a population of cells allowed to differentiate in culture had 1 ring/cell (n=987).

These results demonstrate that midbody scars distribute preferentially rather than randomly, and that dividing cells, e.g., stem cells, accumulate midbody scars at a much greater rate than differentiated cells. Therefore, midbody scars are useful markers for dividing cells, e.g., stem or progenitor cells.

Example 6

Identification of Stem Cells in Tissue Culture

Cells are fixed with formaldehyde or methanol using standard protocols and then stained with one or more antibodies to proteins listed in Table 1. A fluor-labeled primary antibody is used, or alternatively a labeled secondary antibody is added to visualize the primary. Standard immunofluorescence methods are then used to image the midbody scars.

Example 7

Identification of Stem Cells in Tissue Sections

To identify stem cells in paraffin or frozen tissue sections, the sections are labeled with one or more antibodies as described herein. Then, a secondary antibody is used, e.g., a secondary antibody coupled to horse radish peroxidase (for paraffin sections) or coupled to a fluorescent probe (for frozen sections). Then, the sections are washed and the presence of midbody scars detected using known methods appropriate for the secondary antibody used.

Example 8

Isolating Midbody Scars

Known midbody isolation procedures can be adapted for use on mitotic cells to interphase cells to isolate midbody scars. These methods are preferably used on cells with high numbers of midbody scars; these cells can be selected as described herein, e.g., using a cell line stably expressing GFP-MKLP1, a midbody scar marker to label the scars. Cells with high numbers of midbody scars can be isolated by flow cytometry using known cytometry techniques. The methods can include depolymerizing the actin (e.g., using cytochalasin B) and/or microtubule network (e.g., nocodazole) to release the midbody scars from the plasma membrane.

MKLP1 is degraded in mitotic cells except for the midbody scar-associated fraction, which persists in interphase cells. Midbody scars are isolated by affinity chromatography, e.g., using antibodies to a polypeptide component of the midbody scars or to GFP, with or without additional biochemical methods to enrich for midbody scars, such as sucrose gradients, and gel filtration.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting the presence of a midbody scar in a mammalian cell, the method comprising:

contacting a mammalian cell suspected to have a midbody scar with an antibody or antigen-binding portion thereof that binds specifically to a polypeptide component of a midbody scar selected from the group consisting of mitotic kinesin-like protein 1 (MKLP1), Epsilon tubulin ($\epsilon$-tubulin), Centrosomal Protein 55 kDa (Cep55), and Aurora B kinase;

detecting binding of the antibody to its antigen; and identifying a midbody scar in the mammalian cell if binding of the antibody to its antigen is detected in a ring structure not at a midbody or centrosome, thereby detecting a midbody scar.

2. The method of claim 1, comprising:

contacting the mammalian cell with two or more antibodies or antigen-binding portions thereof that each bind specifically to a polypeptide component of a midbody scar, and detecting binding of the two or more antibodies, wherein colocalized binding of the two or more of antibodies indicates the presence of a midbody scar.

3. The method of claim 2, wherein the polypeptide is selected from the group consisting of mitotic kinesin-like protein 1 (MKLP1); Epsilon tubulin ($\epsilon$-tubulin); Centrosomal Protein 55 kDa (Cep55); and Aurora B kinase.

4. The method of claim 1, wherein the cell is in interphase.

5. The method of claim 1, wherein the mammalian cell is a fixed cell.

6. The method of claim 5, wherein the fixed cell is in a pathology specimen.

7. The method of claim 1, wherein the cell is in tissue.

8. The method of claim 1, wherein the antibody or antigen-binding portion thereof is bound or linked to a detectable moiety.

9. The method of claim 8, wherein detecting binding of the antibody to its antigen comprises detecting the detectable moiety.

10. The method of claim 1, wherein the ring structure is about 2 μm in diameter.

11. The method of claim 1, wherein the ring structure is localized adjacent to the plasma membrane.

12. The method of claim 1, wherein the ring structure is determined not to comprise detectable gamma tubulin.

* * * * *